United States Patent
Patek et al.

(10) Patent No.: US 11,090,433 B2
(45) Date of Patent: Aug. 17, 2021

(54) SYSTEM AND METHOD FOR BODY MASS INDEX RELATION TO PATIENT DIFFERING PSYCHOLOGICAL STRESS EFFECT ON BLOOD GLUCOSE DYNAMICS IN PATIENTS WITH INSULIN DEPENDENT DIABETES

(71) Applicant: University of Virginia Patent Foundation, Charlottesville, VA (US)

(72) Inventors: Stephen D. Patek, Charlottesville, VA (US); Basak Ozaslan, Charlottesville, VA (US); Linda Gonder-Frederick, Charlottesville, VA (US)

(73) Assignee: UNIVERSITY O VIRGINIA PATENT FOUNDATION, Charlottesville, VA (US)

( * ) Notice: Subject to any disclaimer, the term of this patent is extended or adjusted under 35 U.S.C. 154(b) by 179 days.

(21) Appl. No.: 16/485,989

(22) PCT Filed: Feb. 15, 2018

(86) PCT No.: PCT/US2018/018403
§ 371 (c)(1),
(2) Date: Aug. 14, 2019

(87) PCT Pub. No.: WO2018/152349
PCT Pub. Date: Aug. 23, 2018

(65) Prior Publication Data
US 2020/0230319 A1  Jul. 23, 2020

Related U.S. Application Data

(60) Provisional application No. 62/459,096, filed on Feb. 15, 2017.

(51) Int. Cl.
*A61M 5/172* (2006.01)
*G16H 20/17* (2018.01)
(Continued)

(52) U.S. Cl.
CPC ...... *A61M 5/1723* (2013.01); *A61M 5/14276* (2013.01); *G16H 20/17* (2018.01);
(Continued)

(58) Field of Classification Search
CPC .................. A61M 5/1723; A61M 5/14244; G16H 50/20; G16H 50/30; G16H 20/17;
(Continued)

(56) References Cited

U.S. PATENT DOCUMENTS

2005/0272640 A1   12/2005  Doyle, III et al.
2011/0208027 A1   8/2011   Wagner et al.
(Continued)

FOREIGN PATENT DOCUMENTS

WO    2016-201120 A1   12/2016

OTHER PUBLICATIONS

Y. Nakadate et al., "Body Mass Index Predicts Insulin Sensitivity During Cardiac Surgery: A Prospective Observational Study", Canadian Journal of Anaesthesia/Journal Canadien D'Anesthesie, Feb. 12, 2018, pp. 551-559, vol. 65, No. 5, XP036700569.
(Continued)

*Primary Examiner* — Manuel A Mendez
(74) *Attorney, Agent, or Firm* — Buchanan Ingersoll & Rooney PC

(57) ABSTRACT

An insulin device configured to control insulin dispensing based on insulin sensitivity. The insulin device includes a processor configured to receive insulin dosing schedule information, psychological stress level data, and body mass index (BMI) data; a sensor configured to generate a blood glucose level measurement. The sensor is calibrated as a function of the psychological stress level data and the BMI data and the processor is configured to monitor and detect changes of the blood glucose level measurement that are determined to have occurred as a function of changes of the
(Continued)

psychological stress level data, and identify a time when the BMI data counteracts a detected change in the blood glucose level measurement. The insulin device also includes an insulin dispensing valve controlled by the processor to change the insulin dosing schedule information in accordance with the counteracting BMI data.

13 Claims, 7 Drawing Sheets

(51) Int. Cl.
  *G16H 50/30* (2018.01)
  *G16H 50/70* (2018.01)
  *A61M 5/142* (2006.01)
(52) U.S. Cl.
  CPC ............ *G16H 50/30* (2018.01); *G16H 50/70* (2018.01); *A61M 2205/3553* (2013.01); *A61M 2205/3569* (2013.01); *A61M 2205/3584* (2013.01); *A61M 2230/201* (2013.01)
(58) Field of Classification Search
  CPC . A61B 5/14532; A61B 5/7275; A61B 5/4839; A61K 38/28
  See application file for complete search history.

(56) References Cited

U.S. PATENT DOCUMENTS

| | | |
|---|---|---|
| 2012/0088989 A1 | 4/2012 | Bousamra et al. |
| 2015/0217053 A1 | 8/2015 | Booth et al. |
| 2015/0289821 A1 | 10/2015 | Rack-gomer et al. |
| 2015/0289823 A1* | 10/2015 | Rack-Gomer ........ A61B 5/1118 600/365 |
| 2016/0354543 A1 | 12/2016 | Cinar et al. |

OTHER PUBLICATIONS

The extended European Search Report dated Nov. 10, 2020, by the European Patent Office in corresponding European Application No. 18753776.6. (8 pages).

International Search Report (PCT/ISA/210) dated Apr. 16, 2018, by the U.S. Patent and Trademark Office as the International Searching Authority for International Application No. PCT/US2018/018403.

Written Opinion (PCT/ISA/237) dated Apr. 16, 2018, by the U.S. Patent and Trademark Office as the International Searching Authority for International Application No. PCT/US2018/018403.

* cited by examiner

SYSTEM AND METHOD FOR BODY MASS INDEX RELATION TO PATIENT DIFFERING PSYCHOLOGICAL STRESS EFFECT ON BLOOD GLUCOSE DYNAMICS IN PATIENTS WITH INSULIN DEPENDENT DIABETES

RELATED APPLICATION

This application claims the benefit under 35 U.S.C. § 119 of U.S. Provisional Patent No. 62/459,096 filed on Feb. 15, 2017, the entire contents of which is hereby incorporated by reference in its entirety.

STATEMENT REGARDING FEDERALLY SPONSORED RESEARCH OR DEVELOPMENT

This disclosure was made with government support under Grant No. DK106826 awarded by the National Institutes of Health. The U.S. government has certain rights in the disclosure.

FIELD

An aspect of an embodiment of the present disclosure provides a device, method, and computer readable medium to control dispensing of insulin based on insulin sensitivity.

BACKGROUND INFORMATION

In patients with insulin dependent diabetes (T1DM), better management of the disease requires accounting for as many factors as possible that can affect blood glucose (BG) during a day. Psychological stress is not a part of current insulin regimen design while it is known to have effects on endocrine system by changes in secretion of glucocorticoids, catecholamine, growth hormone and prolactin. (see document "[1]" Ranabir).

The impact of stress on blood glucose level has been investigated previously and results were various. In a review published in 1985, Carter et al. put the results from three of their previous studies together to evaluate the reaction of blood glucose levels to increased stress in patients with type I diabetes. The results showed that it was not possible to infer a stress induced hyperglycemia in these patients. Therefore, they concluded that the assumption of hyperglycemia occurrence in the presence of stress needs to be avoided in T1DM treatment arrangement (see document "[2]" Patek). In 1990, Halford et al. reported a significant patient-specific stress effect for half of the 15 patients in the study who showed an increase in blood glucose levels. Authors inferred that stress was influential on blood glucose levels at least in some patients with diabetes (see document "[3]" "Clinical guidelines on the identification, evaluation, and treatment of overweight and obesity in adults: executive summary. Expert Panel on the Identification, Evaluation, and Treatment of Overweight in Adults.,"). In another study published in 1990, a significant blood glucose response to psychological stress was found and the type and magnitude of the response were observed to be affected by idiosyncratic factors (see document "[4]" Carter et al.). Later in 2000, Kramer et al. published a study where the results supported the existence of a metabolic disturbance by stress with an idiosyncratic variability in T1DM patients (see document "[5]" Halford et al). Finally, in Gonder-Frederick et al.'s recent study using the same data with this study, it was reported that psychological stress affects BG and the direction and magnitude were patient specific (see document "[6]" Gonder-Frederick et al).

The techniques described here consider insulin sensitivity to be a time-varying physiological parameter and utilizes continuous glucose monitoring and insulin delivery data to quantify insulin sensitivity of the patient over time. Further, insulin sensitivity can be used for tracking the state of the patient's condition and adjust the treatment plans so that the appropriate treatment regime is applied to a patient.

BACKGROUND REFERENCES

The following patents, applications and publications as listed below and throughout this document are hereby incorporated by reference in their entirety herein (and which are not admitted to be prior art with respect to the present disclosure by inclusion in this section):

[1] S. Ranabir and K. Reetu, "Stress and hormones," *Indian J. Endocrinol. Metab.*, vol. 15, no. 1, pp. 18-22, 2011.

[2] S. Patek, D. Lv, E. A. Ortiz, C. Hughes-Karvetski, S. Kulkarni, Q. Zhang, and M. D. Breton, "Empirical Representation of Blood Glucose Variability in a Compartmental Model," in *Prediction Methods for Blood Glucose Concentration*, Springer International Publishing, 2015, pp. 133-156.

[3] "Clinical guidelines on the identification, evaluation, and treatment of overweight and obesity in adults: executive summary. Expert Panel on the Identification, Evaluation, and Treatment of Overweight in Adults.," *Am. J. Clin. Nutr.*, vol. 68, no. 4, pp. 899-917, October 1998.

[4] W. R. Carter, L. A. Gonder-Frederick, D. J. Cox, W. L. Clarke, and D. R. Scott, "Effect of Stress on Blood Glucose in IDDM," *Diabetes Care*, vol. 8, no. 4, pp. 411-412, July 1985.

[5] W. K. Halford, S. Cuddihy, and R. H. Mortimer, "Psychological stress and blood glucose regulation in type I diabetic patients," *Health Psychol. Off. J. Div. Health Psychol. Am. Psychol. Assoc.*, vol. 9, no. 5, pp. 516-528, 1990.

[6] L. A. Gonder-Frederick, W. R. Carter, D. J. Cox, and W. L. Clarke, "Environmental stress and blood glucose change in insulin-dependent diabetes mellitus," *Health Psychol. Off. J. Div. Health Psychol. Am. Psychol. Assoc.*, vol. 9, no. 5, pp. 503-515, 1990.

[7] J. R. Kramer, J. Ledolter, G. N. Manos, and M. L. Bayless, "Stress and metabolic control in diabetes mellitus: methodological issues and an illustrative analysis," *Ann. Behav. Med. Publ. Soc. Behav. Med.*, vol. 22, no. 1, pp. 17-28, 2000.

[8] L. A. Gonder-Frederick, J. H. Grabman, B. Kovatchev, S. Patek, A. Basu, J. E. Pinsker, Y. C. Kudva, C. A. Wakeman, E. Dassau, C. Cobelli, H. C. Zisser, and F. C. Doyle III, "Is Psychological Stress a Factor for Incorporation Into Future Closed-Loop Systems?," *J. Diabetes Sci. Technol.*, 2016.

[9] J. A. O. C, R. Gomez-Perez, G. Arata-Bellabarba, and V. Villaroel, "Relationship Between Bmi, Total Testosterone, Sex Hormone-Binding-Globulin, Leptin, Insulin and Insulin Resistance in Obese Men," *Arch. Androl.*, vol. 52, no. 5, pp. 355-361, January 2006.

[10] A. Lukanova, E. Lundin, A. Zeleniuch-Jacquotte, P. Muti, A. Mure, S. Rinaldi, L. Dossus, A. Micheli, A. Arslan, P. Lenner, R. E. Shore, V. Krogh, K. L. Koenig, E. Riboli, F. Berrino, G. Hallmans, P. Stattin, P. Toniolo, and R. Kaaks, "Body mass index, circulating levels of sex-steroid hormones, IGF-I and IGF-binding protein-3: a cross-sectional study in healthy women," *Eur. J. Endocrinol.*, vol. 150, no. 2, pp. 161-171, February 2004.

[11] I. Kyrou and C. Tsigos, "Stress hormones: physiological stress and regulation of metabolism," *Curr. Opin. Pharmacol.*, vol. 9, no. 6, pp. 787-793, December 2009.

[12] A. Moan, A. Høieggen, G. Nordby, I. Os, I. Eide, and S. E. Kjeldsen, "Mental stress increases glucose uptake during hyperinsulinemia: associations with sympathetic and cardiovascular responsiveness," Metabolism., vol. 44, no. 10, pp. 1303-1307, October 1995.

[13] T. Touma, S. Takishita, Y. Kimura, H. Muratani, and K. Fukiyama, "Mild mental stress increases insulin sensitivity in healthy young men," *Clin. Exp. Hypertens. N. Y. N* 1993, vol. 18, no. 8, pp. 1105-1114, November 1996.

[14] G. Seematter, E. Guenat, P. Schneiter, C. Cayeux, E. Jéquier, and L. Tappy, "Effects of mental stress on insulin-mediated glucose metabolism and energy expenditure in lean and obese women," *Am. J. Physiol. Endocrinol. Metab.*, vol. 279, no. 4, pp. E799-805, October 2000.

[15] P. G. Kopelman, A. Grossman, P. Lavender, G. M. Besser, L. H. Rees, and D. Coy, "The cortisol response to corticotrophin-releasing factor is blunted in obesity," *Clin. Endocrinol.* (Oxf.), vol. 28, no. 1, pp. 15-18, January 1988.

[16] M. Vranic, "Banting Lecture: Glucose Turnover: A Key to Understanding the Pathogenesis of Diabetes (Indirect Effects of Insulin)," *Diabetes*, vol. 41, no. 9, pp. 1188-1206, September 1992.

The following patents, applications and publications as listed below and throughout this document are hereby incorporated by reference in their entirety herein. It should be appreciated that various aspects of embodiments of the present method, system, devices, article of manufacture, computer readable medium, and compositions may be implemented with the following methods, systems, devices, article of manufacture, computer readable medium, and compositions disclosed in the following U.S. Patent Applications, U.S. Patents, and PCT International Patent Applications and are hereby incorporated by reference herein and co-owned with the assignee (and which are not admitted to be prior art with respect to the present disclosure by inclusion in this section):

A. International Patent Application No. PCT/US2017/015616 entitled "METHOD, SYSTEM, AND COMPUTER READABLE MEDIUM FOR VIREALIZATION OF A CONTINUOUS GLUCOSE MONITORING TRACE", filed Jan. 30, 2017.

B. International Patent Application No. PCT/US2016/058234 entitled "System, Method and Computer Readable Medium for Dynamical Tracking of the Risk for Hypoglycemia in Type 1 and Type 2 Diabetes", filed Oct. 21, 2016.

C. International Patent Application No. PCT/US2016/054200 entitled "GAIT PATHOLOGY DETECTION AND MONITORING SYSTEM, AND METHOD", filed Sep. 28, 2016.

D. International Patent Application No. PCT/US2016/050109 entitled "SYSTEM, METHOD, AND COMPUTER READABLE MEDIUM FOR DYNAMIC INSULIN SENSITIVITY IN DIABETIC PUMP USERS", filed Sep. 2, 2016; U.S. patent application Ser. No. 15/255,828 entitled "SYSTEM, METHOD, AND COMPUTER READABLE MEDIUM FOR DYNAMIC INSULIN SENSITIVITY IN DIABETIC PUMP USERS", filed Sep. 2, 2016.

E. U.S. patent application Ser. No. 15/252,365 entitled "Method, System and Computer Readable Medium for Predictive Hypoglycemia Detection for Mild to Moderate Exercise", filed Aug. 31, 2016.

F. U.S. patent application Ser. No. 15/109,682 entitled "Central Data Exchange Node For System Monitoring and Control of Blood Glucose Levels in Diabetic Patients", filed Jul. 5, 2016; Publication No. US-2016-0331310-AI, Nov. 17, 2016; International Patent Application No. PCT/US2015/010167 entitled "Central Data Exchange Node For System Monitoring and Control of Blood Glucose Levels in Diabetic Patients", filed Jan. 5, 2015; Publication No. WO2015103543, Jul. 9, 2015.

G. International Patent Application No. PCT/US2016/036729 entitled "CGM Based Fault Detection and Mitigation of Insulin Delivery/Monitoring Systems Via Metabolic State Tracking", filed Jun. 9, 2016; Publication No. WO2016201120, Dec. 15, 2016.

H. International Patent Application No. PCT/US2016/036481 entitled "Hemoglobin A1c and Self-Monitored Average Glucose: Validation of the Dynamical Tracking eA1c Algorithm in Type 1 Diabetes", filed Jun. 8, 2016; Publication No. WO2016200970, Dec. 15, 2016.

I. International Patent Application No. PCT/US2016/018027 entitled "Method, System and Computer Readable Medium for Assessing Actionable Glycemic Risk", filed Feb. 16, 2016; Publication No. WO2016133879, Aug. 25, 2016.

J. U.S. patent application Ser. No. 14/902,731 entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; Publication No. US-2016-0171183-A1, Jun. 16, 2016; International Patent Application No. PCT/US2014/045393 entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO2015003124, Jan. 8, 2015.

K. U.S. patent application Ser. No. 14/769,638 entitled "METHOD AND SYSTEM FOR MODEL-BASED TRACKING OF CHANGES IN AVERAGE GLYCEMIA IN DIABETES", filed Aug. 21, 2015; Publication No. US-2016-0004813-A1, Jan. 7, 2016; International Patent Application No. PCT/US2014/017754 entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.

L. International Patent Application No. PCT/US2015/045340 entitled "IMPROVED ACCURACY CONTINUOUS GLUCOSE MONITORING METHOD, SYSTEM, AND DEVICE", filed Aug. 14, 2015; Publication No. WO2016025874, Feb. 18, 2016.

M. U.S. patent application Ser. No. 14/799,329 entitled "Improving the Accuracy of Continuous Glucose Sensors", filed Jul. 14, 2015; Publication No. US-2016-0007890-A1, Jan. 14, 2016; U.S. patent application Ser. No. 12/065,257 entitled "Accuracy of Continuous Glucose Sensors", filed Feb. 28, 2008; Publication No. 2008/0314395, Dec. 25, 2008; International Patent Application No. PCT/US2006/033724 entitled "Method for Improvising Accuracy of Continuous Glucose Sensors and a Continuous Glucose Sensor Using the Same", filed Aug. 29, 2006; Publication No. WO07027691, Mar. 8, 2007.

N. U.S. patent application Ser. No. 14/419,375 entitled "COMPUTER SIMULATION FOR TESTING AND MONITORING OF TREATMENT STRATEGIES FOR STRESS HYPERGLYCEMIA", filed Feb. 3, 2015; Publication No. 2015-0193589, Jul. 9, 2015; International Patent Application No. PCT/US2013/053664 entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.

O. U.S. patent application Ser. No. 14/266,612 entitled "Method, System and Computer Program Product for Real-Time Detection of Sensitivity Decline in Analyte Sensors", filed Apr. 30, 2014; Publication No. 2014/0244216, Aug. 28, 2014; U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014; U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012; International Patent Application No. PCT/US2007/082744 entitled "Method, System and Computer Program Product for Real-Time Detection of Sensitivity Decline in Analyte Sensors", filed Oct. 26, 2007; Publication No. WO/2008/052199, May 2, 2008.

P. U.S. patent application Ser. No. 14/241,383 entitled "Method, System and Computer Readable Medium for Adaptive Advisory Control of Diabetes", filed Feb. 26, 2014; Publication No. 2015-0190098, Jul. 9, 2015; International Patent Application No. PCT/US2012/052422 entitled "Method, System and Computer Readable Medium for Adaptive Advisory Control of Diabetes", filed Aug. 26, 2012; Publication No. WO 2013/032965, Mar. 7, 2013.

Q. U.S. patent application Ser. No. 14/128,922 entitled "Unified Platform For Monitoring and Control of Blood Glucose Levels in Diabetic Patients", filed Dec. 23, 2013; Publication No. 2015/0018633, Jan. 15, 2015; International Patent Application No. PCT/US2012/043910 entitled "Unified Platform For Monitoring and Control of Blood Glucose Levels in Diabetic Patients", filed Jun. 23, 2012; Publication No. WO 2012/178134, Dec. 27, 2012.

R. U.S. patent application Ser. No. 14/128,811 entitled "Methods and Apparatus for Modular Power Management and Protection of Critical Services in Ambulatory Medical Devices", filed Dec. 23, 2013; U.S. Pat. No. 9,430,022, issued Aug. 30, 2016; International Patent Application No. PCT/US2012/043883 entitled "Methods and Apparatus for Modular Power Management and Protection of Critical Services in Ambulatory Medical Devices", filed Jun. 22, 2012; Publication No. WO 2012/178113, Dec. 27, 2012.

S. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; Publication No. 20140046159, Feb. 13, 2014; U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013; International Patent Application No. PCT/US2010/025405 entitled "CGM-Based Prevention of Hypoglycemia via Hypoglycemia Risk Assessment and Smooth Reduction Insulin Delivery", filed Feb. 25, 2010; Publication No. WO 2010/099313 A1, Sep. 2, 2010.

T. International Patent Application No. PCT/US2013/042745 entitled "INSULIN-PRAMLINTIDE COMPOSITIONS AND METHODS FOR MAKING AND USING THEM", filed May 24, 2013; Publication No. WO 2013/177565, Nov. 28, 2013; U.S. Patent Application No. entitled "INSULIN-PRAMLINTIDE COMPOSITIONS AND METHODS FOR MAKING AND USING THEM".

U. U.S. patent application Ser. No. 13/637,359 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016; International Patent Application No. PCT/US2011/029793 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

V. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; Publication No. 2013/0116649, May 9, 2013; International Patent Application No. PCT/US2011/028163 entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.

W. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; Publication No. 2012/0191361, Jul. 26, 2012; International Patent Application No. PCT/US2010/047711 entitled "Tracking the Probability for Imminent Hypoglycemia in Diabetes from Self-Monitoring Blood Glucose (SMBG) Data", filed Sep. 2, 2010; Publication No. WO 2011/028925, Mar. 10, 2011.

X. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; Publication No. 2012/0245556, Sep. 27, 2012; International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; Publication No. WO 2011/028731, Mar. 10, 2011.

Y. U.S. patent application Ser. No. 13/380,839 entitled "System, Method, and Computer Simulation Environment for In Silico Trials in Pre-Diabetes and Type 2 Diabetes", filed Dec. 25, 2011; Publication No. 2012/0130698, May 24, 2012; International Patent Application No. PCT/US2010/040097 entitled "System, Method, and Computer Simulation Environment for In Silico Trials in Prediabetes and Type 2 Diabetes", filed Jun. 25, 2010; Publication No. WO 2010/151834, Dec. 29, 2010.

Z. U.S. patent application Ser. No. 13/322,943 entitled "System Coordinator and Modular Architecture for Open-Loop and Closed-Loop Control of Diabetes", filed Nov. 29, 2011; Publication No. 2012/0078067, Mar. 29, 2012; International Patent Application No. PCT/US2010/036629 entitled "System Coordinator and Modular Architecture for Open-Loop and Closed-Loop Control of Diabetes", filed May 28, 2010; Publication No. WO 2010/138848, Dec. 2, 2010.

AA. U.S. patent application Ser. No. 13/131,467 entitled "Method, System, and Computer Program Product for Tracking of Blood Glucose Variability in Diabetes", filed May 26, 2011; U.S. Pat. No. 9,317,657, issued Apr. 19, 2016; International Patent Application No. PCT/US2009/065725 entitled "Method, System, and Computer Program Product for Tracking of Blood Glucose Variability in Diabetes", filed Nov. 24, 2009; Publication No. WO 2010/062898, Jun. 3, 2010.

BB. U.S. patent application Ser. No. 12/975,580 entitled "Method, System, and Computer Program Product for the Evaluation of Glycemic Control in Diabetes from Self-Monitoring Data", filed Dec. 22, 2010; Publication No. 2012/0004512, Jan. 5, 2012; U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011; U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006; International Patent Application No. PCT/US2001/009884 entitled "Method, System, and Computer Program Product for the Evaluation of Glycemic Control in Diabetes", filed Mar. 29, 2001; Publication No. WO 01/72208, Oct. 4, 2001.

CC. U.S. patent application Ser. No. 12/665,420 entitled "LQG Artificial Pancreas Control System and Related Method", filed Dec. 18, 2009; Publication No. 2010/0249561, Sep. 30, 2010; International Patent Application No. PCT/US2008/067723 entitled "LQG Artificial Pancreas Control System and Related Method", filed Jun. 20, 2008; Publication No. WO 2008/157780, Dec. 24, 2008.

DD. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010; International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.

EE. U.S. patent application Ser. No. 12/664,444 entitled "Method, System and Computer Simulation Environment for Testing of Monitoring and Control Strategies in Diabetes", filed Dec. 14, 2009; Publication No. 2010/0179768, Jul. 15, 2010; International Patent Application No. PCT/US2008/067725 entitled "Method, System and Computer Simulation Environment for Testing of Monitoring and Control Strategies in Diabetes", filed Jun. 20, 2008; Publication No. WO 2008/157781, Dec. 24, 2008.

FF. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013; International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.

GG. U.S. patent application Ser. No. 12/159,891 entitled "Method, System and Computer Program Product for Evaluation of Blood Glucose Variability in Diabetes from Self-Monitoring Data", filed Jul. 2, 2008; Publication No. 2009/0171589, Jul. 2, 2009; International Patent Application No. PCT/US2007/000370 entitled "Method, System and Computer Program Product for Evaluation of Blood Glucose Variability in Diabetes from Self-Monitoring Data", filed Jan. 5, 2007; Publication No. WO07081853, Jul. 19, 2007.

HH. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; Publication No. 2008/0154513, Jun. 26, 2008.

II. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010; International Patent Application No. US2005/013792 entitled "Method, System and Computer Program Product for Evaluating the Accuracy of Blood Glucose Monitoring Sensors/Devices", filed Apr. 21, 2005; Publication No. WO05106017, Nov. 10, 2005.

JJ. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; Publication No. 2005214892, Sep. 29, 2005; International Patent Application No. PCT/US2003/025053 entitled "Managing and Processing Self-Monitoring Blood Glucose", filed Aug. 8, 2003; Publication No. WO 2004/015539, Feb. 19, 2004.

KK. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005; International Patent Application No. US00/22886 entitled "METHOD AND APPARATUS FOR PREDICTING THE RISK OF HYPOGLYCEMIA", filed Aug. 21, 2000; Publication No. WO01/13786, Mar. 1, 2001.

SUMMARY

An insulin device configured to control insulin dispensing based on insulin sensitivity is disclosed, the insulin device comprising a processor configured to receive insulin dosing schedule information, psychological stress level data, and body mass index (BMI) data; a sensor configured to generate a blood glucose level measurement, wherein the sensor is calibrated as a function of the psychological stress level data and the BMI data, and wherein the processor is configured to monitor and detect changes of the blood glucose level measurement that are determined to have occurred as a function of changes of the psychological stress level data, and identify a time when the BMI data counteracts a detected change in the blood glucose level measurement; and an insulin dispensing valve controlled by the processor to change the insulin dosing schedule information in accordance with the counteracting BMI data.

A computer-implemented method to control insulin dispensing based on insulin sensitivity is also disclosed, the method comprising receiving insulin dosing schedule information, psychological stress level data, and body mass index (BMI) data generating a blood glucose level measurement as a function of the psychological stress level data and the BMI data monitoring and detecting changes of the blood glucose level measurement that are determined to have occurred as a function of changes of the psychological stress level data identifying a time when the BMI data counteracts a detected change in the blood glucose level measurement updating the insulin dosing schedule information in accordance with the counteracting BMI data and controlling an insulin dispensing device to provide insulin dosing based on the updated insulin dosing schedule information.

A non-transitory computer readable recording medium encoded with a computer program is disclosed comprising program instructions causing an insulin device to control insulin dispensing based on insulin sensitivity, the program causing the insulin device to receive insulin dosing schedule information, psychological stress level data, and body mass index (BMI) data; generate a blood glucose level measurement as a function of the psychological stress level data and the BMI data; monitor and detect changes of the blood glucose level measurement that are determined to have occurred as a function of changes of the psychological stress level data; identify a time when the BMI data counteracts a detected change in the blood glucose level measurement; update the insulin dosing schedule information in accordance with the counteracting BMI data; and control an insulin dispensing device to provide insulin dosing based on the updated insulin dosing schedule information.

BRIEF DESCRIPTION OF THE DRAWINGS

Other objects and advantages of the present disclosure will become apparent to those skilled in the art upon reading the following detailed description of exemplary embodiments, in conjunction with the accompanying drawings, in which like reference numerals have been used to designate like elements, and in which.

DETAILED DESCRIPTION

Insulin sensitivity, among other factors, depends on the psychological stress of the patient. Additionally, as described herein, the applicant has determined that a change in the stress level for patients with different BMIs does not indicate a common pattern of change in the blood glucose levels. That is, a change in the blood glucose level with a change in stress of different diabetic patients is sporadic. This sporadic phenomenon leads to a less than optimal dosing in patients with different stress levels or patients with frequently changing stress levels.

The present disclosure is directed to providing an improved insulin device method, and computer readable medium configured to control insulin dispensing based on insulin sensitivity. The device includes a computer configured to administer insulin to a patient in a more effective manner by considering a previously uncorrelated relationship between the body mass index (BMI) and the stress level of the patient. For example, insulin can be dispensed more accurately and precisely to achieve enhanced results with decreased volume. The device uses the foregoing relationship to determine a magnitude and direction of change in the blood glucose levels according to changes in the stress levels. Accordingly, the device changes the insulin dosage in accordance with the change in the blood glucose levels, thereby providing an efficient way of supplying insulin in a more effective manner. For example, to maintain the appropriate blood glucose level, patients with a high stress level and a higher BMI may require less insulin dosage than patients with the same stress level but a lower BMI. In this example, other factors that affect insulin dosage such as meal, physical activity are considered the same for both patients.

Figure 2:
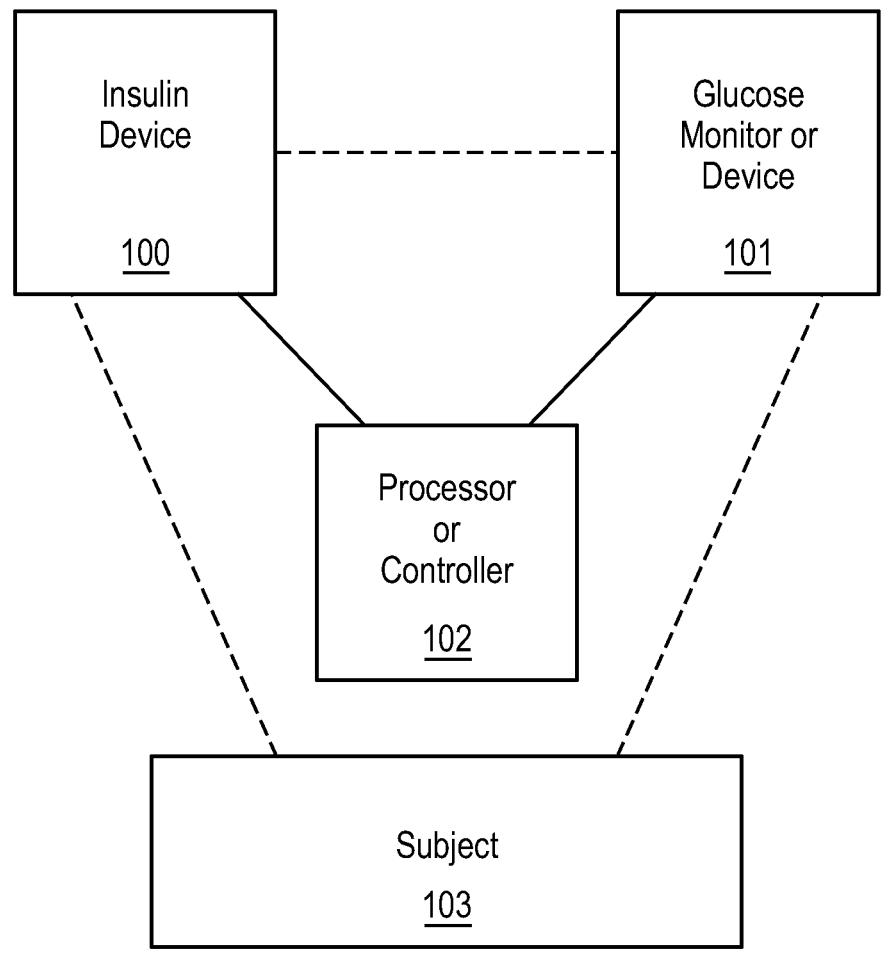
FIG. 2 is a high level functional block diagram of an embodiment of the present disclosure, or an aspect of an embodiment of the present disclosure.

The insulin device includes a processor 102 as illustrated in, for example, FIG. 2 that communicates with the glucose monitor or device 101, and optionally the insulin device 100. The processor or controller 102 is configured to perform the specified calculations. Optionally, the insulin device 100 communicates with the subject 103 to deliver insulin to the subject 103. The processor or controller 102 is configured to perform the specified calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device. The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

The processor 102 is configured to receive insulin dosing schedule information. The insulin dosing schedule information can be inputted using an input device 132 or can be obtained from an insulin pump 10. In an embodiment the insulin pump may be implemented by the subject (or patient) locally at home or other desired location. However, in an alternative embodiment it may be implemented in a clinic setting or assistance setting. For instance, referring to FIG. 5, a clinic setup 158 provides a place for doctors (e.g. 164) or clinician/assistant to diagnose patients (e.g. 159) with diseases related with glucose and related diseases and conditions.

The processor 102 is configured to receive psychological stress level data. The psychological stress level is measured on a scale. In an exemplary embodiment, the scale can be 5-point Likert-type scale where 0 represents no stress and 4 represents extreme stress. In a preferred embodiment, the value of the psychological stress level data is 1 on the 5-point Likert-type scale. In another preferred embodiment, the value of the psychological stress level data is 2 on the 5-point Likert-type scale.

The processor 102 is configured to receive body mass index (BMI) data. The BMI data categorizes patients according to clinical guidelines of BMI identification (see document "[8]" (Kramer) into normal BMI, overweight BMI, or obese BMI.

A relationship between psychological stress level and BMI described herein, was identified by a research involving a total of thirty-eight T1DM patients of age range 21-65 years with HbA1c<10% and with use of insulin pump for at least 6 months. Pregnancy, diabetic ketoacidosis or severe hypoglycemia in the 12 months prior to enrollment, history of a seizure disorder, medical conditions and drug use that might interfere with the completion of study was exclusion criteria. Informed consent was obtained from all patients.

Figure 5:
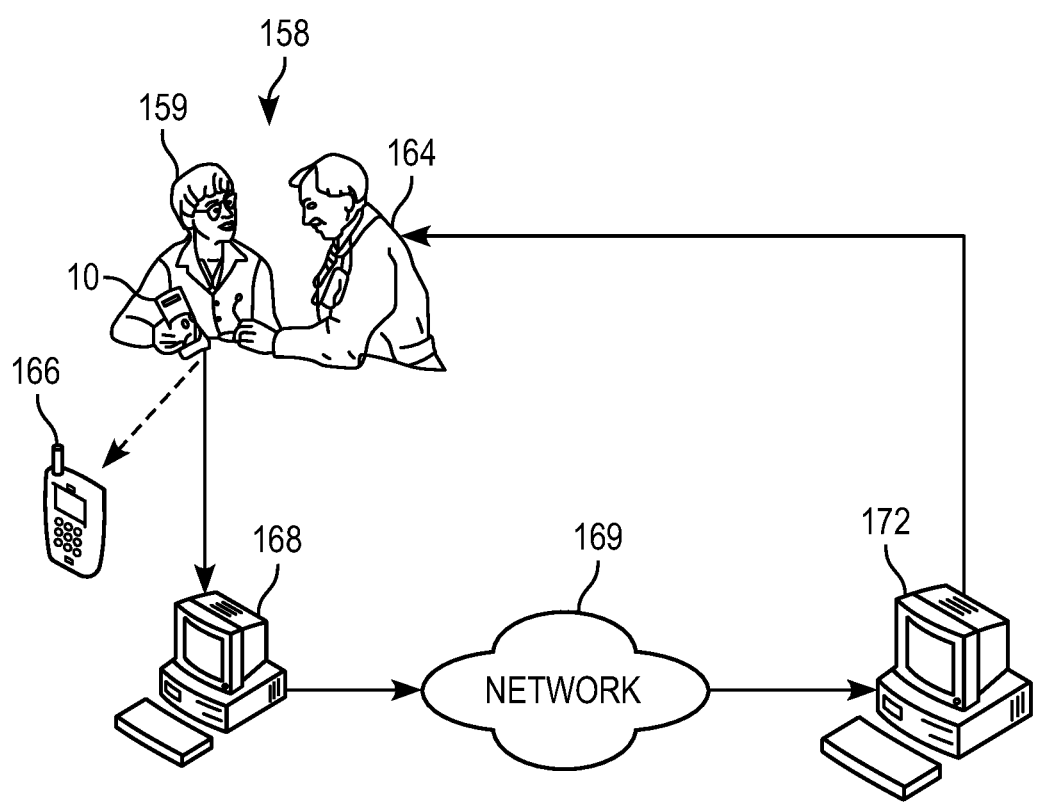
FIG. 5 illustrates a system in which one or more embodiments of the disclosure can be implemented using a network, or portions of a network or computers.

A sensor is configured to generate a blood glucose level measurement, for example, of the patients 159. In an exemplary embodiment, the sensor can be a glucose monitor 101 that communicates with the subject 103 to monitor glucose levels. FIG. 5 illustrates an exemplary system describing an embodiment where the glucose monitor or glucose meter (and/or insulin pump) may be implemented by the subject (or patient) locally at home or other desired location. However, in an alternative embodiment it may be implemented in a clinic setting or assistance setting. For instance, referring to FIG. 5, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the exemplary embodiment and any component thereof may be used in the manner depicted by FIG. 5.

The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling.

Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Figure 3A:
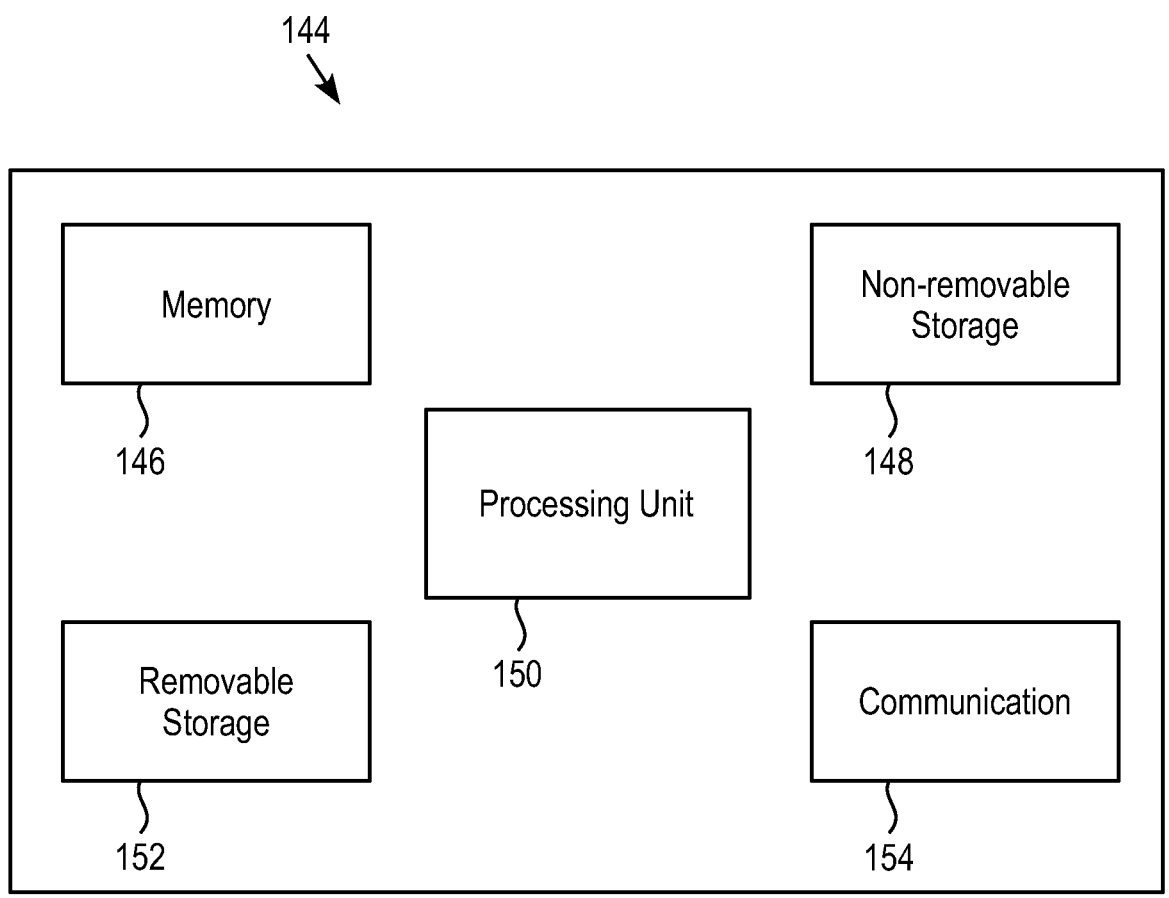
FIG. 3A illustrates a computing device in upon which an embodiment of the disclosure can be implemented.

Embodiments of the disclosure can also be implemented in a standalone computing device associated with the target glucose monitoring device. An exemplary computing device (or portions thereof) 144 in which examples of the disclosure can be implemented is schematically illustrated in FIG. 3A. In an exemplary configuration, computing device 144 can include at least one processing unit 150 and memory 146. Depending on the exact configuration and type of computing device, memory 146 can be volatile (such as RAM), non-volatile (such as ROM, flash memory, etc.) or some combination of the two.

In an exemplary embodiment, the computing device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The computing device 144 may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

The processor 102 is also configured to correlate a detected increase in a value of the psychological stress level data with an increase in a value of the blood glucose level measurement and a detected decrease in a value of the psychological stress level data with a decrease in a value of the blood glucose level measurement. In the research, for each participant, continuous blood glucose monitor (CGM) readings were collected for 7 consecutive days and net effect was computed for all days except the first and last days (mean=5±1 day/patient). Additionally, days with CGM gaps with more than 3 consecutive hours or more than sixty missing CGM values were excluded. Remaining dataset consisted of 188 days from thirty-seven patients with age range 25-62 years (mean=46.8±10.8), HbA1c range 5.7-9.9% (mean=7.4±0.98) and BMI range 21.5-39.4 kg/m² (mean=28.2±4.9).

The sensor is calibrated as a function of the psychological stress level data and the BMI data to recognize the stress effect on glycaemia. To better understand this relationship, the present disclosure provides a variable called "net effect". A change in the net effect implies presence of a factor that affects blood glucose and that this factor is different from meal intake and injected insulin. However, a change in blood glucose itself does not provide enough information to infer whether it is due to a change in eating/bolus behavior or another factor like psychological stress. Therefore, the research further investigated changes in net effect to infer the glycemic effect of daily stress in T1DM patients and found that net effect can take a positive or negative value and it is expected to be around zero for well recorded meal and bolus. The higher the absolute net effect is, the higher the deviation of blood glucose is from its estimated value by the inputs (i.e. meal intake and insulin bolus). More specifically, a negative net effect represents a lower blood glucose occurrence than the estimated value. In the same manner, a positive net effect value represents a higher blood glucose occurrence than the estimate.

Linear mixed effects models were designed to explore (1) net effect mean, (2) total carbohydrate intake and (3) total bolus-carbohydrate intake ratio with patient effect being modeled as random factor where stress and BMI were fixed factors. The reasoning behind net effect concept allowed this model to show whether there is a difference between the real and estimated blood glucose as a result of stress.

To identify this difference, the processor 102 is configured to monitor and detect changes of the blood glucose level measurement that are determined to have occurred as a function of changes of the psychological stress level data and identify a time when the BMI data counteracts a detected change in the blood glucose level measurement. This allows investigating (1) whether glycaemia is affected by stress and (2) whether body mass index is an influential factor on the glycemic effect of stress. Considering possible inaccuracy that might stem from subjectivity in self-evaluation of stress level, the research compared no stress (stress level 0) versus some stress (stress levels 1-2-3-4 combined) before exploring whether the effect differs by stress level. In doing so, factors with p-value less than 0.05 were considered significant. The results identified that stress was not found to result in a common blood glucose pattern towards increase or decrease (p=0.26 for overall stress, p>0.2 for stress levels 1, 2, 3 and 4). Rather, its effect was found to be dependent on body mass index of the patient (p=0.01). Additionally, it was identified that the Stress-BMI interaction had a negative coefficient −7 (p=0.01) opposing the effect of stress that had a positive coefficient 183.16 (p=0.02) (see Table 1).

TABLE 1

Stress Effect (SE) in Relation with BMI

| Parameter | Value | Stress Effect (SE) | p-value |
|---|---|---|---|
| Intercept | −66.11 | 72.03 | 0.36 |
| Stress | 183.16 | 77.93 | 0.02* |
| BMI | 2.07 | 2.43 | 0.40 |
| Stress × BMI | −7.00 | 2.70 | 0.01* |

Another LME model was designed to explore whether the BMIxStress effect differs based on stress level. This time, stress was modeled as originally reported by the patients with values 0 to 4. Results showed significant difference from baseline stress level-0 for both BMIxStress level-1 (p=0.01) and BMIxStress level-2 (p=0.007) (see Table 2).

TABLE 2

Effect of Different Stress Levels on Net Effect Mean in Relation with BMI

| Parameter | Value | Stress Effect (SE) | p-value |
|---|---|---|---|
| Fixed Effects | | | |
| Intercept | −61.44 | 71.66 | 0.39 |
| Stress Level 1 | 204.03 | 86.80 | 0.02* |
| Stress Level 2 | 253.31 | 97.23 | 0.01* |
| Stress Level 3 | −90.28 | 141.50 | 0.52 |
| Stress Level 4 | −302.79 | 255.05 | 0.24 |
| BMI | 1.92 | 2.42 | 0.43 |
| Interaction | | | |
| Stress Level 1 × BMI | −7.86 | 3.05 | 0.01* |
| Stress Level 2 × BMI | −9.43 | 3.47 | 0.007* |
| Stress Level 3 × BMI | 1.97 | 4.76 | 0.68 |
| Stress Level 4 × BMI | 10.78 | 9.18 | 0.24 |

Both models suggest that the processor 102 correlates a counteraction effect by BMI, on the increase of blood glucose with increasing stress, increases with an increase in the value of BMI. That is, the higher the BMI is, the higher the counter effect becomes. The processor 102 also detects that when the increase in the value of the BMI data crosses a threshold, the counteraction results in a decrease in a value of the blood glucose level measurement. That is, after a certain point, counter effect exceeds a threshold and results in a decrease in the blood glucose.

Figure 1:
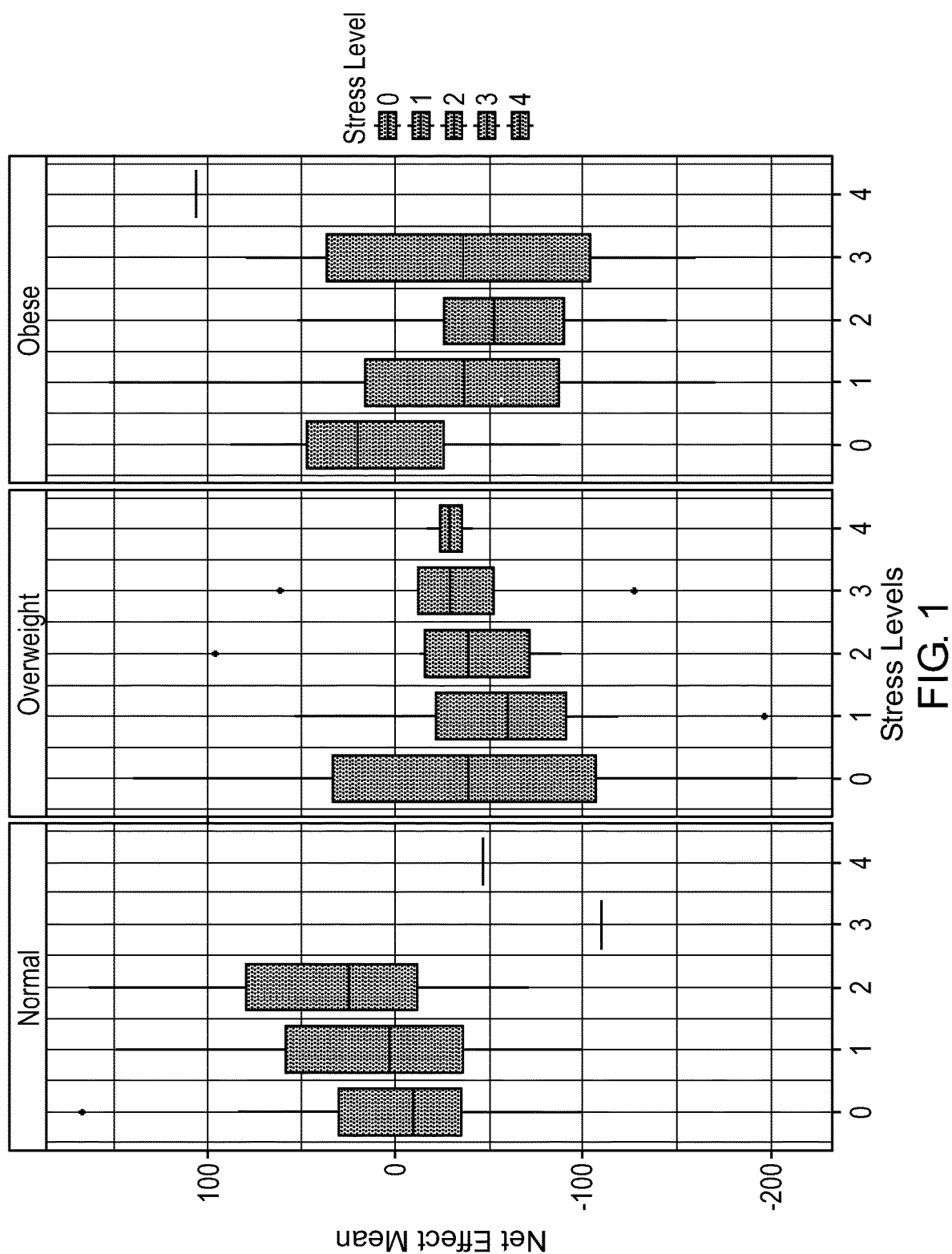
FIG. 1 illustrates the stress effect on Net Effect Mean by BMI categories.

Visualization of data for different BMI categories also supports that the effect of stress on net effect changes based on body mass index (see FIG. 1). This is to say that stress has an effect on blood glucose independent from food intake and insulin injection related changes and this effect is BMI dependent. It also shows that our dataset did not have enough data for stress levels 3&4 at all BMI levels.

Analyses were conducted also only for the days where patients did not exercise (n=103 days) in order to eliminate possible confounding effect of exercise and the same pattern was sustained (p=0.0014 for overall stress, p=0.008 for stress level-1, p=0.004 for stress level-2).

The research also analyzed changes in daily carbohydrate (CHO) intake and daily bolus taken per unit carbohydrate (Total daily bolus/Total CHO intake). 4 days were excluded from the analysis due to no reported carbohydrate intake and LME models were designed for the remained 184-days data. There was no evidence for a change in CHO intake for overall stress (stress levels 1, 2, 3 and 4 combined). However, analyses suggested an increase in daily carbohydrate intake (p=0.03) and a decrease in daily bolus per 1 gr of carbohydrate for stress level-2 (p=0.02) as BMI increases (see Table 3).

TABLE 3

Daily CHO Intake and Insulin Bolus per Unit CHO by Stress Level

| Parameter | Carbohydrate Intake | | | Insulin per 1 gr CHO | | |
|---|---|---|---|---|---|---|
| | Value | SE | p-value | Value | SE | p-value |
| Fixed Effects | | | | | | |
| Intercept | 245.8 | 75.80 | 0.0015 | −0.35 | 0.16 | 0.04 |
| Stress Level 1 | −42.98 | 83.82 | 0.61 | 0.20 | 0.13 | 0.11 |
| Stress Level 2 | −193.33 | 92.93 | 0.04 | 0.02 | 0.14 | 0.03 |
| Stress Level 3 | 19.53 | 132.65 | 0.88 | 0.29 | 0.19 | 0.90 |
| Stress Level 4 | −19.53 | 251.80 | 0.94 | 0.096 | 0.36 | 0.79 |
| BMI | −2.19 | 2.59 | 0.40 | 0.018 | 0.006 | 0.004 |
| Interaction | | | | | | |
| Stress Level 1 × BMI | 2.31 | 2.96 | 0.44 | −0.008 | 0.005 | 0.07 |
| Stress Level 2 × BMI | 7.40 | 3.33 | 0.03 | −0.011 | 0.005 | 0.02 |
| Stress Level 3 × BMI | −0.67 | 4.48 | 0.88 | −0.0016 | 0.007 | 0.8 |
| Stress Level 4 × BMI | 0.23 | 9.33 | 0.98 | −0.0027 | 0.013 | 0.84 |

In an exemplary embodiment, by using the techniques disclosed herein that contemplate the time-varying nature of insulin sensitivity based on the stress level data and the BMI data of a patient, an optimal level of insulin dosage can be administered. In an exemplary embodiment, the insulin dosage can be administered using an insulin dispensing valve that is controlled by the processor 102 to change an insulin dosing schedule in accordance with the counteracting BMI data. In an exemplary embodiment, the insulin dispensing valve has a retractable needle cannula and can be attached to the insulin device. The processor 102 can control the insulin delivered by the insulin dispensing valve to provide an optimal amount to a patient with a particular stress level and BMI. This provides a more appropriate insulin dosage by employing a closed-loop control system as disclosed herein.

In an exemplary embodiment, the processor 102 is configured to correlate the counteraction by the BMI data to a higher uptake of glucose. As such, T1DM and BMI related alterations in endocrine responses and higher increase in energy expenditure with stress in people with higher BMI are responsible for the observed effect. The novelty of this disclosure lies in (1) the use of net effect to examine stress effect on blood glucose by excluding effects of meal and insulin (2) the inclusion of body mass index as a factor to explain a part of the idiosyncratic pattern of stress effect. As described herein, analyses show that body mass index interacts with the stress effect and has a role in the direction and magnitude of its effect. BMI is one of the factors that led to the different observations and conclusion of idiosyncratic responses to mental stress that were reported for patients with T1DM prior to this study.

In addition to a stand-alone computing machine, embodiments of the disclosure can also be implemented on a network system comprising a plurality of computing devices that are in communication with a networking means, such as a network with an infrastructure or an ad hoc network. The network connection can be wired connections or wireless connections.

Figure 3B:
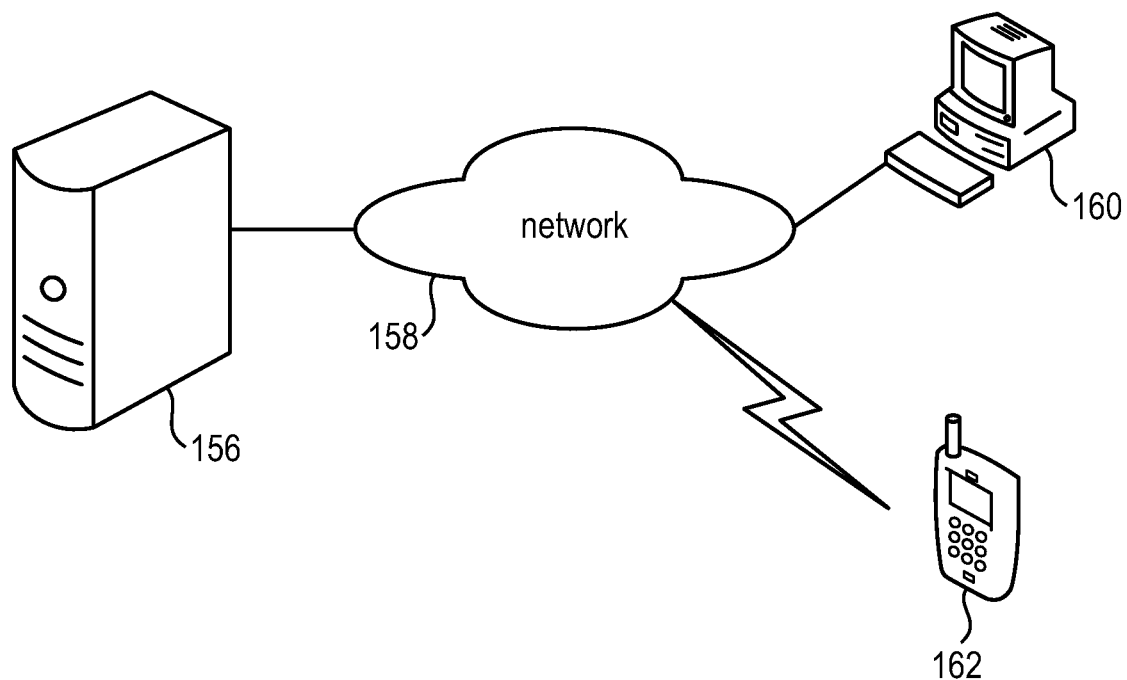
FIG. 3B illustrates a network system in which an embodiment of the disclosure can be implemented.

As a way of example, FIG. 3B illustrates a network system in which embodiments of the disclosure can be implemented. In this example, the network system includes computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non-portable devices) with combinations of such features). In an embodiment, it should be appreciated that the module listed as 156 may be glucose monitor device. In an embodiment, it should be appreciated that the module listed as 156 may be a glucose monitor device (or glucose meter) and/or an insulin device.

Any of the components shown or discussed with FIG. 3B may be multiple in number. The embodiments can be implemented in any of the devices of the system. For example, execution of the instructions or other desired processing can be performed on the same computing device that is any of 156, 160, and 162. Alternatively, an embodiment can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments as disclosed. The processed, encoded or executed software can then be distributed to customers. The distribution can be in a form of storage media (e.g. disk) or electronic copy.

Figure 4:
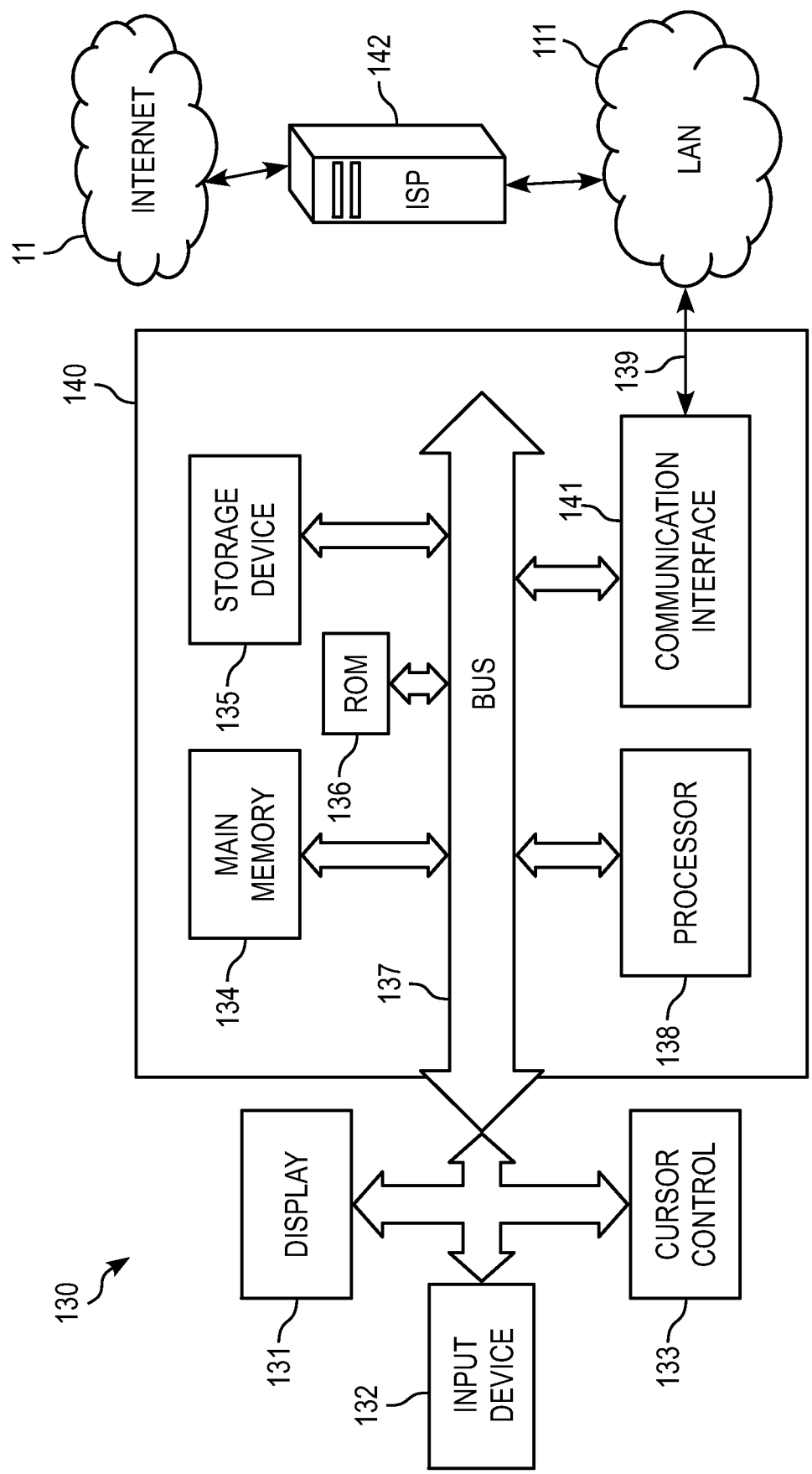
FIG. 4 is a block diagram that illustrates a system including a computer system and the associated Internet connection upon which an embodiment may be implemented.

FIG. 4 is a block diagram that illustrates a system 130 including a computer system 140 and the associated Internet 11 connection upon which an embodiment may be implemented. Such configuration can be used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 4. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices.

Note that while FIG. 4 illustrates various components of a computer system, it is not intended to represent any particular architecture or manner of interconnecting the components; as such details are not germane to the present disclosure. It will also be appreciated that network computers, handheld computers, cell phones and other data processing systems which have fewer components or perhaps more components may also be used. The computer system of FIG. 4 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. The computer system 140 can include an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device can, for example, have two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments disclosed are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that include bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line.

As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 can include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 can provide data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of method and system for virtualization of virtual basal rates from planned and historical insulin delivery have been developed and disclosed herein; and may be implemented and utilized with the related processors, networks, computer systems, internet, and components and functions according to the schemes disclosed herein.

Figure 6:
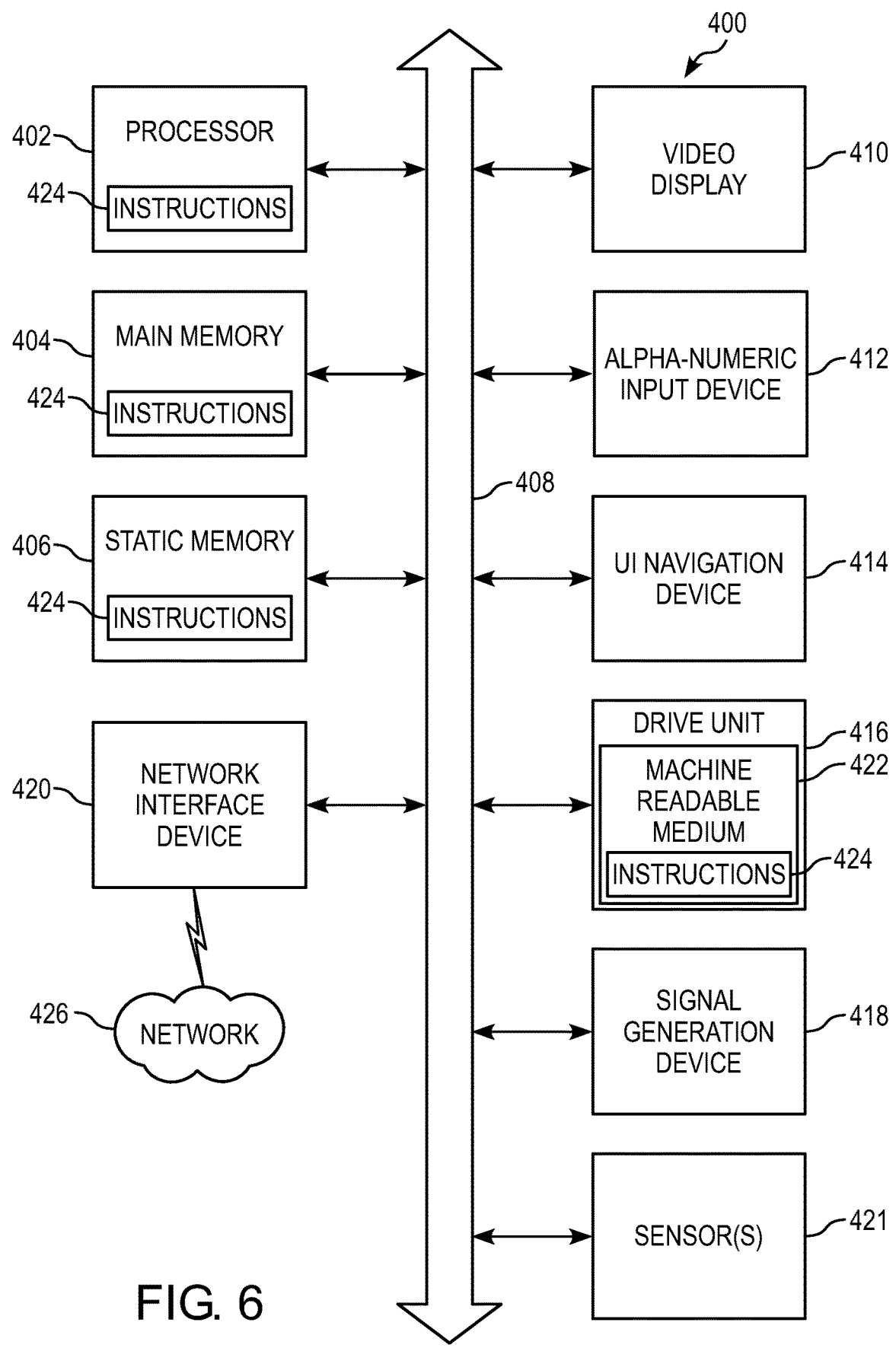
FIG. 6 is a block diagram illustrating an example of a machine upon which one or more aspects of embodiments of the present disclosure can be implemented.

FIG. 6 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can include dedicated circuitry or logic that is specifically configured to perform one or more techniques such as discussed above, such as including a special-purpose processor, a field programmable gate array (FPGA) or an application-specific integrated circuit (ASIC). In an example, a circuit can include programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits include a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can include processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

An exemplary machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that any of the components or modules referred to with regards to any of the present exemplary embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

In summary, while the present disclosure has been described with respect to specific embodiments, many modifications, variations, alterations, substitutions, and equivalents will be apparent to those skilled in the art. The present disclosure is not to be limited in scope by the specific embodiment described herein. Indeed, various modifications of the present disclosure, in addition to those described herein, will be apparent to those of skill in the art from the foregoing description and accompanying drawings. Accordingly, the exemplary embodiment is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is descried herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

What is claimed is:

1. An insulin device configured to control insulin dispensing based on insulin sensitivity, the insulin device comprising:
   a processor configured to receive insulin dosing schedule information, psychological stress level data, and body mass index (BMI) data;
   a sensor configured to generate a blood glucose level measurement, wherein the sensor is calibrated as a function of the psychological stress level data and the BMI data, and wherein the processor is configured to:
      monitor and detect changes of the blood glucose level measurement that are determined to have occurred as a function of changes of the psychological stress level data, and
      identify a time when the BMI data counteracts a detected change in the blood glucose level measurement; and
   an insulin dispensing valve controlled by the processor to change the insulin dosing schedule information in accordance with the counteracting BMI data.

2. The insulin device of claim 1, wherein the insulin dosing schedule information is input.

3. The insulin device of claim 1 in combination with:
an insulin pump, wherein the insulin dosing schedule information is received from the insulin pump.

4. The insulin device of claim 1, wherein the psychological stress level data is measured on a scale.

5. The insulin device of claim 4, wherein the scale is a five point Likert scale.

6. The insulin device of claim 1, wherein the processor is configured to correlate a detected increase in a value of the psychological stress level data with an increase in a value of the blood glucose level measurement.

7. The insulin device of claim 1, wherein the processor is configured to correlate a detected decrease in a value of the psychological stress level data with a decrease in a value of the blood glucose level measurement.

8. The insulin device of claim 1, wherein the processor is configured to correlate a counteraction of a BMI data increase with an increase in a value of the BMI data.

9. The insulin device of claim 8, wherein the processor is configured to detect a decrease in a value of a blood glucose level measurement data when the increase in the value of the BMI data crosses a threshold.

10. The insulin device of claim 1, wherein the processor is configured to correlate the counteraction by a BMI data with a higher uptake of glucose.

11. The insulin device of claim 1 in combination with:
a display, wherein the processor is configured to categorize and display the BMI data as normal BMI, overweight BMI, or obese BMI.

12. A computer-implemented method to control insulin dispensing based on insulin sensitivity, the method comprising:
receiving insulin dosing schedule information, psychological stress level data, and body mass index (BMI) data;
generating a blood glucose level measurement as a function of the psychological stress level data and the BMI data;
monitoring and detecting changes of the blood glucose level measurement that are determined to have occurred as a function of changes of the psychological stress level data;
identifying a time when the BMI data counteracts a detected change in the blood glucose level measurement;
updating the insulin dosing schedule information in accordance with the counteracting BMI data; and
controlling an insulin dispensing device to provide insulin dosing based on the updated insulin dosing schedule information.

13. A non-transitory computer readable recording medium encoded with a computer program comprising program instructions causing an insulin device to control insulin dispensing based on insulin sensitivity, the program causing the insulin device to:
receive insulin dosing schedule information, psychological stress level data, and body mass index (BMI) data;
generate a blood glucose level measurement as a function of the psychological stress level data and the BMI data;
monitor and detect changes of the blood glucose level measurement that are determined to have occurred as a function of changes of the psychological stress level data;
identify a time when the BMI data counteracts a detected change in the blood glucose level measurement;
update the insulin dosing schedule information in accordance with the counteracting BMI data; and
control an insulin dispensing device to provide insulin dosing based on the updated insulin dosing schedule information.

* * * * *